(12) United States Patent
Wood et al.

(10) Patent No.: US 6,547,681 B1
(45) Date of Patent: Apr. 15, 2003

(54) DEVICE AND METHOD FOR FITTING GOLF CLUBS FOR USE IN SAND

(75) Inventors: Donald C. Wood, Temecula, CA (US); Todd D. Harman, Long Beach, CA (US)

(73) Assignee: Roger Cleveland Golf Company, Inc., Cypress, CA (US)

( * ) Notice: Subject to any disclaimer, the term of this patent is extended or adjusted under 35 U.S.C. 154(b) by 0 days.

(21) Appl. No.: 09/599,835

(22) Filed: Jun. 23, 2000

Related U.S. Application Data
(60) Provisional application No. 60/141,312, filed on Jun. 25, 1999.

(51) Int. Cl.[7] ............................................. A63B 69/36
(52) U.S. Cl. ........................ 473/405; 473/409; 473/278
(58) Field of Search ................................ 473/405, 407, 473/409, 278, 131

(56) References Cited

U.S. PATENT DOCUMENTS

| | | | | |
|---|---|---|---|---|
| 4,130,283 A | * | 12/1978 | Lindquist | |
| 4,955,611 A | * | 9/1990 | Moller | |
| 5,356,147 A | * | 10/1994 | MacDonald | |
| 5,398,418 A | * | 3/1995 | Jones | |
| 6,156,396 A | * | 12/2000 | Florian | |

* cited by examiner

Primary Examiner—Paul T. Sewell
Assistant Examiner—Nini F. Legesse
(74) Attorney, Agent, or Firm—Parkhurst & Wendel, L.L.P.

(57) ABSTRACT

A method of determining a bounce fitting for a golf club for use in sand for a particular golfer, by determining the relative hardness of golf course bunker sand in which the tests are conducted, having a golfer hit a golf ball from that sand thereby forming a divot, measuring the length of the divot, determining the relative depth of the divot, and correlating the divot length, divot depth and sand hardness to determine a desired bounce fitting. The divot length is measured with a device for designating a certain location from which a golf ball is to be hit and for measuring the length of a divot caused by hitting a golf ball from that location.

12 Claims, 5 Drawing Sheets

FIG. 5A
HARD SAND

| DIVOT DEPTH | DIVOT LENGTH | | |
|---|---|---|---|
| | 0-2" | 2-5" | >5" |
| SHALLOW | LB | LB | LB |
| MEDIUM | LB | LB | MB |
| DEEP | LB | MB | MB |

FIG. 5B
MEDIUM SAND

| DIVOT DEPTH | DIVOT LENGTH | | |
|---|---|---|---|
| | 0-2" | 2-5" | >5" |
| SHALLOW | LB | LB | MB |
| MEDIUM | LB | MB | MB |
| DEEP | LB | MB | HB |

FIG. 5C
SOFT SAND

| DIVOT DEPTH | DIVOT LENGTH | | |
|---|---|---|---|
| | 0-2" | 2-5" | >5" |
| SHALLOW | LB | LB | MB |
| MEDIUM | LB | MB | HB |
| DEEP | MB | HB | HB |

DEVICE AND METHOD FOR FITTING GOLF CLUBS FOR USE IN SAND

CROSS-REFERENCE TO RELATED APPLICATIONS

This application claims the benefit of the Jun. 25, 1999 filing date of U.S. Provisional Patent Application Ser. No. 60/141,312.

FIELD OF THE INVENTION

This invention relates to custom-fitting wedge-type golf clubs for use in sand to a particular golf player, to a unique device for use in such club fitting, and to a method for using that unique device.

BACKGROUND OF THE INVENTION

Since different individual golfers will have different height, leg length, arm length, body configuration, swings, and swing actions, it is well known that to function properly, golf clubs should be "fitted" to the individual player. Proper fitting will result in a "prescription" which will uniquely characterize a particular golf club or set of golf clubs so that they will function properly when hit by the golfer whom that prescription fits. Among the variables which may be specified in such a golf club prescription are total club length, shaft type and flex, grip size, golf club head design and lie angle.

Additionally, for golf clubs which are intended for use in playing shots from sand traps or bunkers, which clubs are typically known as sand irons or sand wedges, the size and shape of the sole of the clubhead and the resultant "bounce" of the clubhead from sand in a golf course sand bunker are important aspects of sand wedge clubhead design and sand wedge fitting.

Further, the fitting of sand wedges or other clubs often used for sand shots may vary depending upon sand conditions as well as other aspects of clubhead design and player swing characteristics. Sand wedge fitting choices, such as selection of a sand wedge having a certain sole width and thus bounce properties, and certain choices concerning where to place the ball in the player's stance, how open or closed to have the face of the sand wedge at impact with the ball, and how to swing the sand wedge, are in part based upon the characteristics of the sand at or near the location where the player's ball rests in a sand bunker.

More accurate knowledge concerning the characteristics of the sand upon which the player's ball lies assists experienced sand players during practice sessions in more accurately making an appropriate clubhead design selection and in determining stance/ball location, club face position and swing strength in executing a sand shot from a particular lie in a particular sand trap. A club fitter having some knowledge of relative characteristics of sand, determined by a standard testing technique, in which test swings are made as a basis for fitting an appropriate sand iron to a particular player, will facilitate a fitting which is more likely to be advantageous for that player.

Heretofore, there have been few, if any, objective methods of analyzing a golf player's habitual sand divot characteristics, or methods for standardized testing of sand in golf course sand bunkers to further understand a player's habitual sand divot characteristics. And, there have been few, if any, methods for analyzing sand divot characteristics and correlating the results of such analyses with proper sand wedge bounce characteristics, for facilitating fitting a player with a sand wedge having optimum bounce characteristics for that player.

BRIEF SUMMARY OF THE INVENTION

Thus, it is an object of the present invention to overcome the above-discussed problems and needs unsatisfied by the prior art.

It is a further object of the present invention to provide a sand divot gauge capable of measuring the relative length of sand divots created by a player's shots from a golf course sand trap.

Another object of the present invention is to provide a system for correlating the characteristics of golf course bunker sand, such as its hardness, fluffiness, or bulk density, and particularly such sand wherein sand divot tests are performed, with the results of such sand divot testing to provide an objective indication of sand wedge bounce characteristics preferable for that player.

Other objects and further features of the present invention are described hereafter in this specification.

In a first embodiment, an advantageous sand divot gauge of the present invention comprises a planar, and preferably transparent, mat to one edge of which are pivotally attached a golf ball placement indicator and a sand divot length gauge for pivotally overlying a sand divot after a golf ball has been hit from the location specified by the golf ball placement indicator.

In a second embodiment, an advantageous sand gauge of the present invention comprises a planar, and preferably transparent, mat which, within its area, includes a golf ball placement hole through which a golf ball may be placed at a specified test location in golf course bunker sand, and a sand divot length gauge extending rearwardly along a divot path from the golf ball placement location to indicate the length of a sand divot created when a golf ball is hit from sand at the location specified by the golf ball placement opening.

BRIEF DESCRIPTION OF THE DRAWINGS

The aforementioned embodiments and further features of the advantageous system of the present invention are illustrated and further explained in conjunction with the following drawings, wherein:

FIG. 5A is a table showing desired sand wedge bounce characteristics derived from a player's practice or test sand divot length and divot depth in relatively hard sand;

FIG. 5B is a table showing desired sand wedge bounce characteristics derived from a player's practice or test sand divot length and divot depth in relatively medium density sand;

FIG. 5C is a table showing desired sand wedge bounce characteristics derived from a player's practice or test sand divot length and divot depth in relatively soft sand.

DETAILED DESCRIPTION

Figure 1:
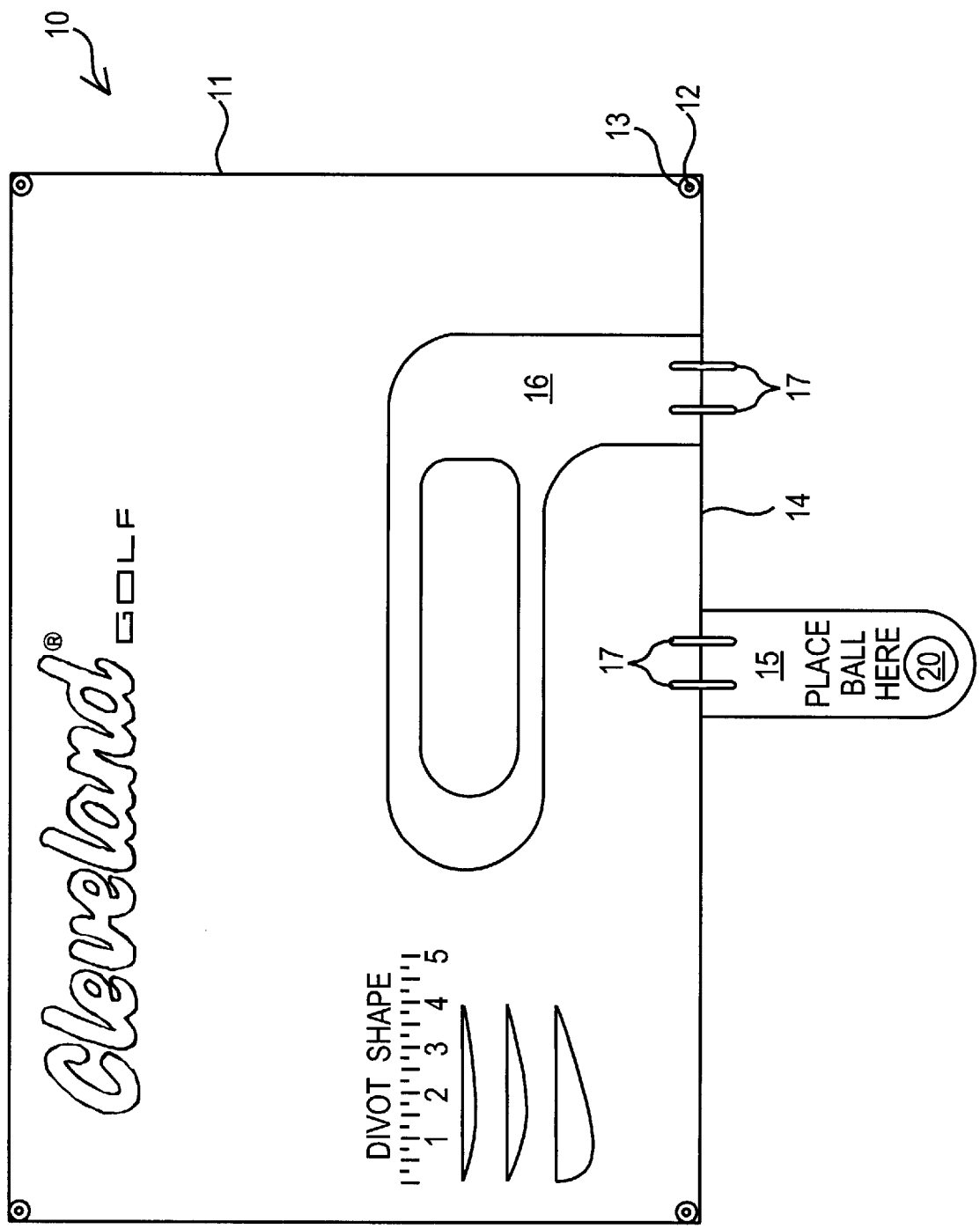
FIG. 1 is a plan or top view of a first embodiment of the advantageous sand divot length gauge of the present invention showing the ball placement indicator in extended position.
Figure 2:
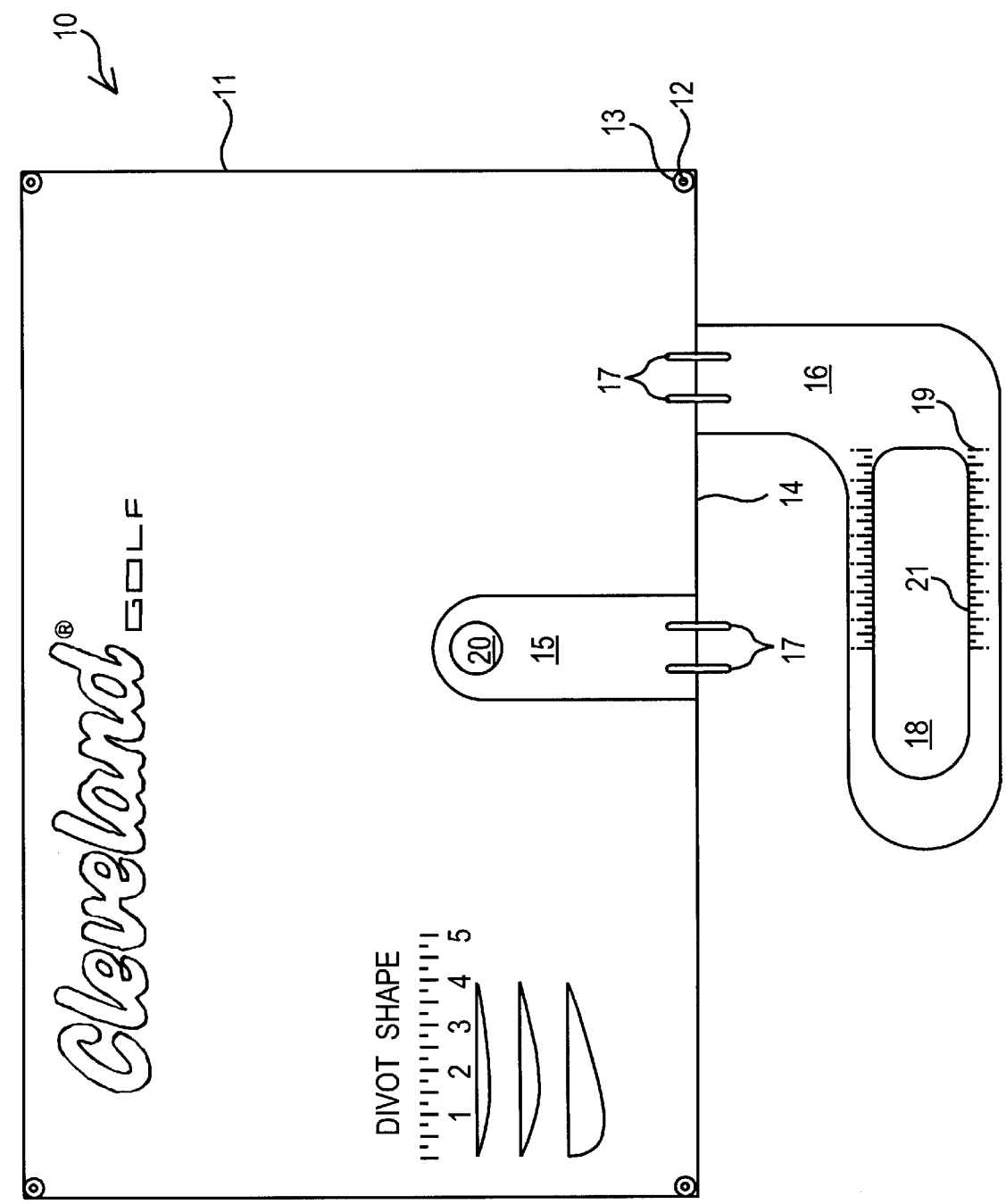
FIG. 2 is a plan or top view of the embodiment of the advantageous sand divot length gauge of FIG. 1 showing the sand divot length gauge in extended position.
Figure 3:
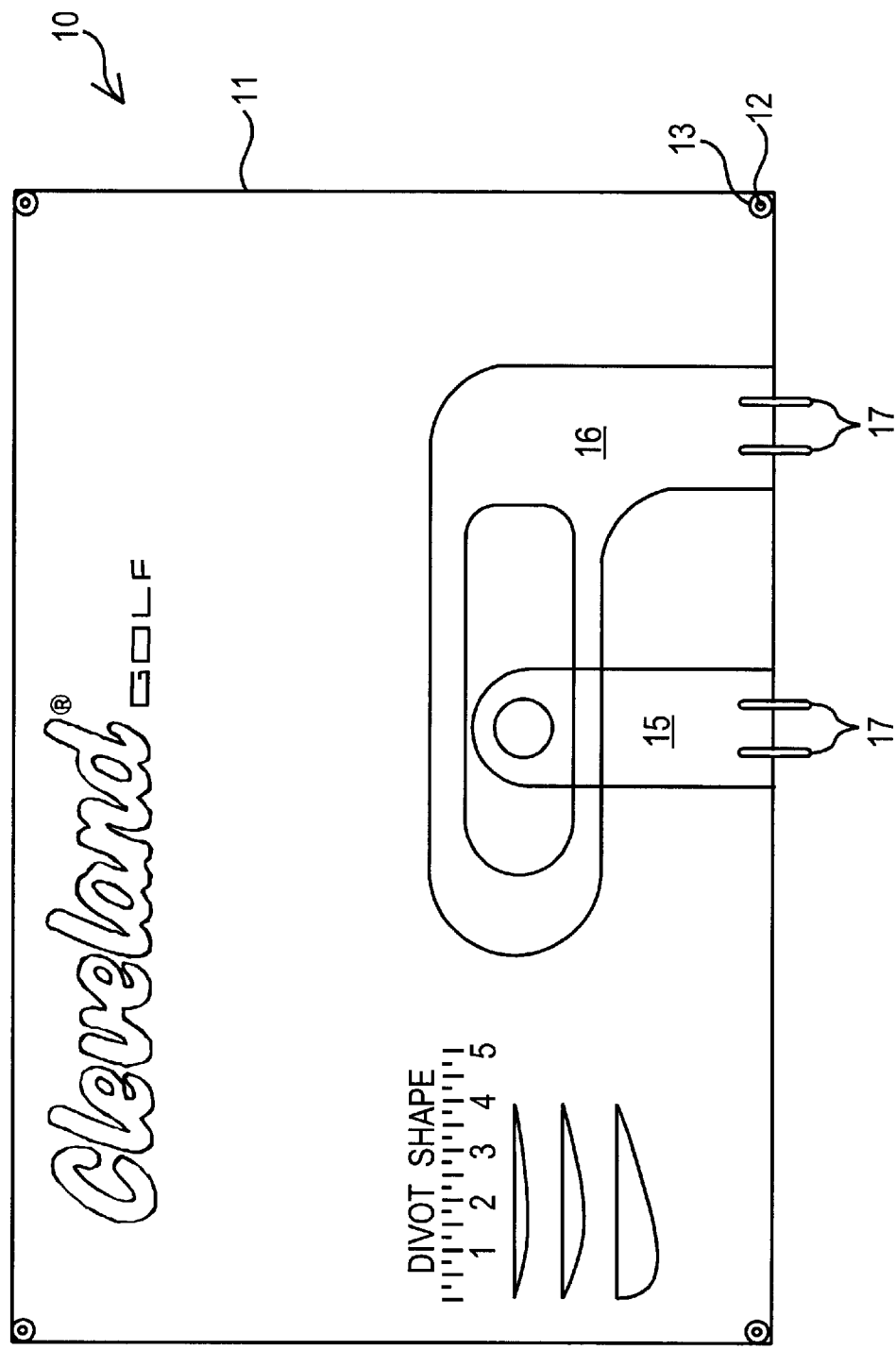
FIG. 3 is a plan or top view of the embodiment of the advantageous sand divot length gauge of FIG. 1 showing both the ball placement indicator and sand divot length gauge pivotally folded back on the planar area of the device.

A first embodiment of the advantageous sand divot gauge of the present invention is illustrated in FIGS. 1–3, and primarily comprises a thin planar mat of material having ball location and sand divot length gauge members, tabs or flaps pivotally attached to one edge thereof. As illustrated in FIG. 1, the sand divot gauge 10 comprises thin stabilizing mat 11 which may be a mat of transparent material, such as transparent vinyl, or other plastic or glassy material. Mat 11 is relatively thin and may be of a thickness of about 1/16th of an inch, and may have planar dimensions of, for example, approximately 16×24 inches, although any suitable thickness and dimensions may be used. As illustrated in FIGS. 1–3, each corner of mat 11 includes a hole 12 which may or may not include a grommet 13. This hole is for having a pin, such as a relatively long golf tee, thrust there-through and pushed into golf course bunker sand below, to stabilize or maintain the position of mat 11 in golf course bunker sand.

Pivotally or foldably attached to lower edge 14 of mat 11 are golf ball location flap 15 and sand divot length measurement gauge flap 16, the back side of which is illustrated in FIGS. 1 and 3, and the front side of which is illustrated in FIG. 2. Flaps 15 and 16 are attached to edge 14 of mat 11 by any suitable means permitting folding pivotal movement thereof from a position folded onto the area of mat 11, like sand divot length gauge 16 is illustrated in FIG. 1, to a substantially coplanar extended position outside the area of mat 11, like ball location tab 15 is illustrated in FIG. 1. In the embodiment illustrated in FIGS. 1–3, tabs 15 and 16 are pivotally connected to mat 11 by metal or plastic ring-like members 17.

The reference numerals appearing in FIGS. 2 and 3 identify the same parts identified by the same reference numerals in FIG. 1.

FIG. 2 shows the device of FIG. 1 in the mode wherein ball location tab 15 is folded back onto the area of mat 11, while sand divot length gauge flap 16 is extended outwardly from lower edge 14 of mat 11. As shown in FIG. 2, sand divot length gauge 16 includes opening 18 for overlying a divot in golf course sand bunker sand, and includes graduated length measurement indicia 19 which commence, at their left end in the view shown in FIG. 2, along a line which includes the center point of circular opening 20 in ball location tab 15 so that the zero point 21 of the measurement indicia 19 corresponds to the approximate location of the center of a ball located within opening 20 of ball location tab 15 when used in the mode illustrated in FIG. 1. Thus measurement indicia 19 extend from zero point 21 to the right in the view illustrated in FIG. 2, to measure the length of a sand divot underlying divot measurement flap 16. Measurement indicia 19 may be printed onto, etched into, or molded into the surface of the device by any suitable method.

It will be appreciated that the device as illustrated in FIGS. 1–3 is constructed primarily for use with right-handed golfers who would be making a divot in relationship to mat 11 at about the location of sand divot length measurement tab 16 as illustrated in FIG. 2, the ball having been struck in the direction of the left edge of FIG. 2, and the length of the divot extending rightwardly from about zero point 21 throughout a length measurable on measurement indicia 19. However, it will also be appreciated that when the device is constructed using transparent material for mat 11 and tabs 15 and 16, the device is equally usable for a left-handed golfer by simply turning the mat over and using the opposite side from that illustrated in FIGS. 1–3.

In use, the advantageous sand divot length gauge as illustrated in FIGS. 1–3 is first placed in the condition illustrated in FIG. 3 wherein both tabs 15 and 16 are folded onto the area of mat 11, by placing mat 11 at a desired location in a golf club sand bunker or in some other practice volume of sand bunker sand. Two or more corners of mat 11 may be secured by pushing a relatively long golf tee or other spike-like member through holes 12 to thereby stabilize or maintain mat 11 and gauge 16 in the desired location vis-a-vis the location of a ball initially placed in opening 20 of tab 15 as illustrated in FIG. 1. Then, ball location tab 15 is pivoted or folded outwardly to the location illustrated in FIG. 1, and a golf ball is placed in opening 20, whereupon tab 15 is returned to its initial location as illustrated in FIG. 3.

After a practice ball has been located in the designated location, as explained above, the player takes his stance, addressing the ball, without touching the sand, and hits the shot, leaving a sand divot extending rearwardly from the location where the ball had been placed. The length of that divot is then measured by pivotally folding divot length tab 16 outwardly to the position illustrated in FIG. 2 and determining the length of the divot corresponding to the numbered measurement indicia 19 extending rightwardly from zero point 21 on divot length measurement tab 16.

Additionally, the relative depth of that sand divot is also assessed. For example, the device of FIGS. 1–3 also includes in approximately its lower left corner, certain divot-shaped indicia which first include indicia in the nature of a ruler, and therebelow representations of the cross-sectional shapes of sand divots of relatively shallow, relatively medium, and relatively deep depth, top to bottom, respectively.

For each test sand divot evaluated, the divot length is recorded, and the corresponding relative divot depth is also recorded. To confirm the accuracy of the divot length/divot depth data, a golfer being so tested will typically repeat the above-described procedure several times until reasonably reproducible results of repetitive divot length/divot depth results are achieved, which reasonably reproducible results likely represent a typical sand divot for that player.

Additionally, the relative hardness or bulk density of the sand in which the sand divot lengths and depths are being recorded is also determined, for example by using a gauge for testing golf course and sand bunker sand such as that described in our copending U.S. patent application Ser. No. 09/603,434, filed Jun. 23, 2000 the entire disclosure of which is hereby incorporated by reference. For the purposes of this application use of such sand gauges or the like may be termed evaluating the apparent bulk hardness of golf course sand bunker sand. It will be appreciated that a virtually identical golf swing using the same club, here a sand wedge, will produce a sand divot of a somewhat different length/depth combination when used to play a ball from sand having different hardness or bulk density characteristics.

A sand gauge, described in our copending U.S. patent application Ser. No. 09/603,434, comprises an outer housing wherein a combination probe shaft and gauge is mounted, and a spring is mounted for compression between the housing and the probe shaft to regulate load on the probe shaft. The device is used by pushing its lower probe end into the sand bunker sand being tested, and stop pushing the device toward the sand when the bottom of the outer housing contacts the sand, recording the probe displacement at that moment. The depth to which the spike is driven into the sand is a measure of the softness or bulk density of the sand.

It is also well known to those experienced in playing golf shots from golf course sand bunkers that sand irons or sand wedges having increased amounts of so-called "bounce" perform more efficiently and effectively in softer, less dense (by volume), sand, than sand irons or sand wedges having lesser bounce characteristics. The "bounce" of a golf club may be described as a golf club's ability to repel the ground surface. The amount of bounce of a golf club may be a function of a combination of: the width of that club's sole, the angle between the leading edge of the club and the low point on the sole in relation to the ground plane, the overall roundness of the sole from leading edge to trailing edge and amount of leading edge break. Sand wedge designs may vary in one or all of these elements. A wedge that repels the ground surface strongly is said to have "high bounce" characteristics, and will often feature a wider sole dimension and greater angle than other wedges between the leading edge and sole low point in relation to the ground plane. A wedge that repels the ground surface slightly is said to have "low bounce" characteristics, and may feature a narrower sole width and less angle than other wedges between the leading edge and low point on the sole in relation to the ground plane.

The present inventors have found that by correlating the relative hardness, i.e., apparent bulk hardness, of the sand in which sand divot tests are conducted, with the relative divot depth and relative divot length of sand divots made in such sand, a reliable system for fitting a player making such practice or test divots with a sand iron or sand wedge having desirable bounce characteristics can be achieved. Tables relating sand divot length and divot depth created in each of relatively hard, medium and soft sands, are illustrated in FIGS. 5A, B and C, respectively. Those figures show the inventors' observed results for prescribing relatively low bounce (LB), medium bounce (MB), or high bounce (HB) sand wedges for golfers who produce sand divots of different divot lengths and depths in each of relatively hard, medium and soft golf course bunker sand samples, respectively.

Figure 4:
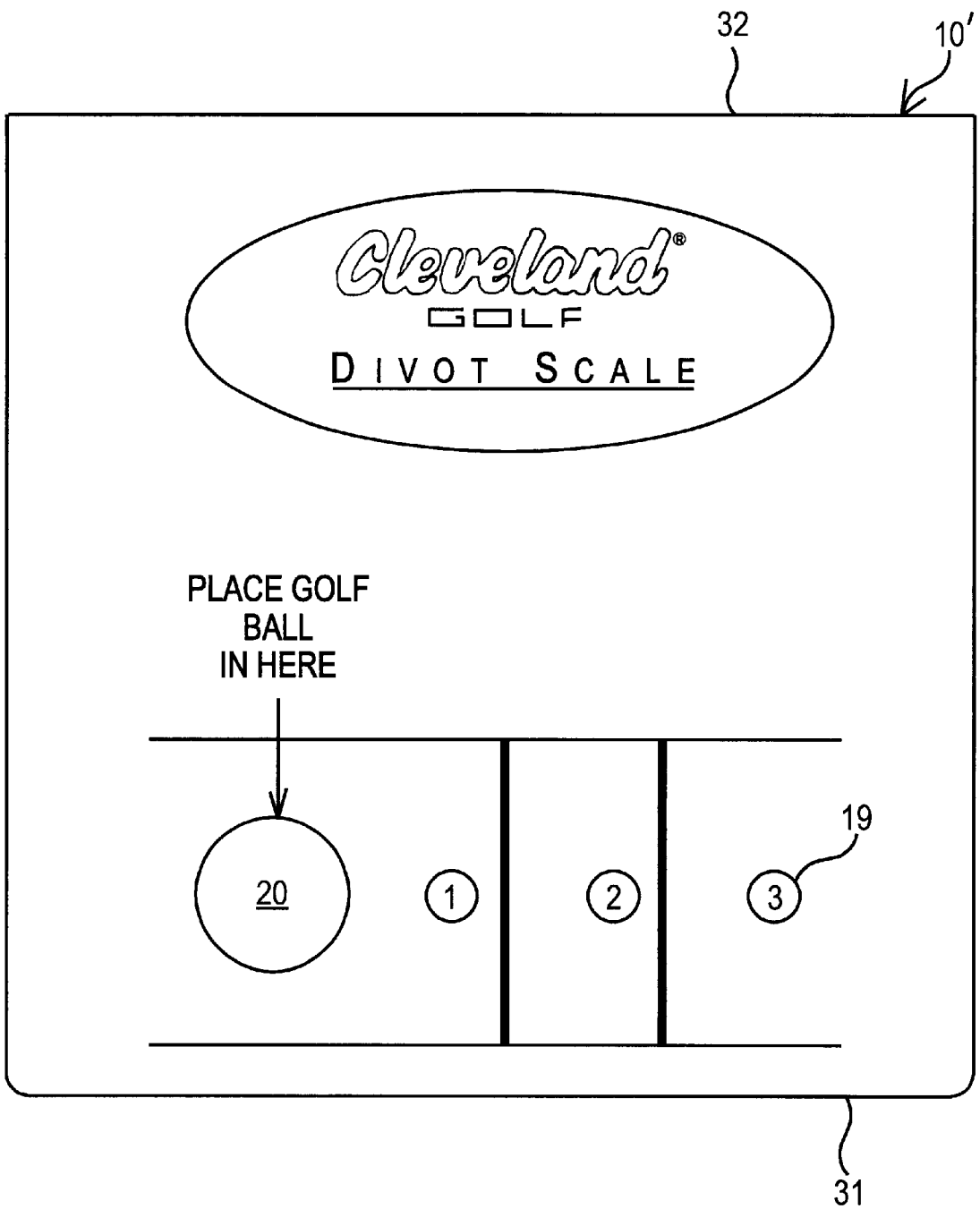
FIG. 4 is a plan view of another embodiment of an advantageous sand divot length gauge of the present invention.

Another embodiment of the advantageous sand divot length gauge of the present invention is illustrated in FIG. 4, wherein the device 10' comprises a mat 31, which again may be made of relatively thin, transparent material, and which has dimensions, for example, of approximately 12×12 inches, although any suitable thickness and dimensions may be used. In this embodiment, ball locating hole 20 is within the area of primary mat 31, and sand divot length measurement indicia 19 again extend to the right from the location of ball locator opening 20. However, in this embodiment the divot length indicia 19 simply comprise markings indicating one of three divot length ranges, here designated regions 1, 2 and 3, respectively, which may, for example, comprise ranges of divot lengths corresponding to 0 to 2 inches, 2 to 5 inches, and greater than 5 inches, respectively, although the particular divot length ranges, measured from the center of ball locator opening 20, may be modified, depending upon the particular divot length gauge designer's beliefs, or for example, based upon the relative hardness of the sand conditions in which such sand divot gauge may often be used.

The device of FIG. 4, like the device illustrated in FIGS. 1–3, is shown for use in measuring the sand divot length of divots created by a right handed golfer, although when the device is constructed on a transparent mat 31, it need merely be turned over to be equally useful for left handed players.

Additionally, top edge 32 of the embodiment illustrated in FIG. 4 may be foldably connected to one or more additional anchoring pieces which may be anchored in the sand by pushing a relatively long golf tee or other spike-like device there-through or through holes therein to establish a fixed position for the device in use.

In use, mat 31 of the device illustrated in FIG. 4 is placed in a desired location on golf course bunker sand, and a test golf ball is located in opening 20. Mat 31 is then raised, for example by pivotally folding about an axis substantially corresponding with upper edge 32, and a right-handed golfer hits a golf ball located in a location corresponding to location 20 in a direction toward the left edge of the device as illustrated in FIG. 4, thus creating a divot extending at least to the right of the location corresponding to opening 20.

Mat 31 is then pivotally lowered back into its initial location where upon the three measurement indicia regions indicated by numerals 19 overlie the area of the sand divot created by hitting the ball formerly located in opening 20, and the relative length of that divot is determined corresponding to which of the three designated measurement regions corresponds to the location of the right end of the divot. That relative length is then recorded. Additionally, the relative divot depth of the same divot is also recorded. The test procedure is then repeated until it becomes clear that for the test player's swing from the sand in which the divot length/depth tests are being conducted, the resultant divot length/depth results are substantially repeatable. Then, a desired sand wedge bounce prescription can readily be determined from the inventive relationships among sand hardness, divot length, divot depth and bounce, as illustrated in one of FIG. 5A, B, or C.

While the advantageous sand divot length gauges of the present invention and corresponding methods of using same, have been illustrated in specific preferred embodiments herein, those skilled in the art will understand that various modifications of the advantageous gauges of the present invention may be made without departing from the scope and spirit of the invention as stated in the following claims.

What is claimed is:

1. A method of determining a bounce fitting for a sand iron-type golf club for a particular golfer, comprising:
   determining the relative apparent bulk hardness of golf course sand bunker sand in which bounce fitting tests are conducted;
   have a particular golfer hit at least one golf ball from said sand thereby forming a divot in the sand;
   measuring the length of said divot;
   determining the relative depth of said divot;
   and correlating the divot length, divot depth and apparent bulk sand hardness to determine a desired bounce fitting for a sand iron-type golf club for the particular golfer.

2. The method of claim 1 wherein the relative apparent bulk sand hardness is determined to be one of hard, medium or soft sand.

3. The method of claim 1 wherein the relative divot depth is determined to be one of shallow, medium or deep divot depth.

4. The method of claim 1 wherein the divot length is determined to be in one of a plurality of different length ranges.

5. The method of claim 4 wherein the divot length is determined to be in one of three different length ranges of about 0 to x; x to y; or greater than y, where $x < y \leq 6$ inches in length.

6. The method of claim 5 wherein the divot length is determined to be in one of the ranges of about 0 to 2 inches; 2 to 5 inches; or greater than 5 inches, in length.

7. The method of claim 1 wherein the particular golfer hits a plurality of golf balls from said sand thereby forming a plurality of divots in the sand;

determining an average length of said plurality of divots, and determining an average relative depth of said plurality of divots;

and determining a desired bounce fitting from said average divot depth and average divot length.

8. The method of claim 7 wherein determining a desired bounce fitting among LB meaning low bounce, MB meaning medium bounce and HB meaning high bounce of said iron-type golf club, is carried out by comparing the apparent bulk sand hardness, average divot depth and average divot length with the data in one of a Hard Sand Table, a Medium Sand Table, and a Soft Sand Table, wherein, said Hard Sand Table comprises:

|  | DIVOT LENGTH | | |
| --- | --- | --- | --- |
| DIVOT DEPTH | 0–2" | 2–5" | >5" |
| Shallow | LB | LB | LB |
| Medium | LB | LB | LB |
| Deep | LB | MB | MB | said Medium Sand Table comprises:

|  | DIVOT LENGTH | | |
| --- | --- | --- | --- |
| DIVOT DEPTH | 0–2" | 2–5" | >5" |
| Shallow | LB | LB | LB |
| Medium | LB | LB | LB |
| Deep | LB | MB | MB | said Soft Sand Table comprises:

|  | DIVOT LENGTH | | |
| --- | --- | --- | --- |
| DIVOT DEPTH | 0–2" | 2–5" | >5" |
| Shallow | LB | LB | MB |
| Medium | LB | MB | MB |
| Deep | MB | HB | HB. |

9. The method of claim 1 wherein determining a desired bounce fitting among LB meaning low bounce, MB meaning medium bound and HB meaning high bounce of a sand iron-type golf club, is carried out by comparing the apparent bulk sand hardness, divot depth and divot length with the data in one of a Hard Sand Table, a Medium Sand Table, and a Soft Sand Table, wherein, said Hard Sand Table comprises:

said Medium Sand Table comprises;

|  | DIVOT LENGTH | | |
| --- | --- | --- | --- |
| DIVOT DEPTH | 0–2" | 2–5" | >5" |
| Shallow | LB | LB | LB |
| Medium | LB | LB | LB |
| Deep | LB | MB | MB | said Medium Sand Table comprises:

|  | DIVOT LENGTH | | |
| --- | --- | --- | --- |
| DIVOT DEPTH | 0–2" | 2–5" | >5" |
| Shallow | LB | LB | MB |
| Medium | LB | MB | MB |
| Deep | LB | MB | HB | said Soft Table comprises:

|  | DIVOT LENGTH | | |
| --- | --- | --- | --- |
| DIVOT DEPTH | 0–2" | 2–5" | >5" |
| Shallow | LB | LB | LB |
| Medium | LB | MB | HB |
| Deep | MB | HB | HB. |

10. The method of claim 9 wherein the apparent bulk sand hardness is hard sand, and the desired bounce fitting is determined from said Hard Sand Table.

11. The method of claim 9 wherein the apparent bulk sand hardness is medium sand, and the desired bounce fitting is determined from said Medium Sand Table.

12. The method of claim 9 wherein the apparent bulk sand hardness is soft sand, and the desired bounce fitting is determined from said Soft Sand Table.

* * * * *